US009492952B2

United States Patent
Luong-Van et al.

(10) Patent No.: US 9,492,952 B2
(45) Date of Patent: Nov. 15, 2016

(54) SUPER-HYDROPHILIC STRUCTURES (75) Inventors: Emma Kim Luong-Van, Singapore (SG); Isabel Rodriguez, Singapore (SG); Hong Yee Low, Botannia (SG); Noha Elmouelhi, Randolph, NJ (US); Kevin Cooper, Flemington, NJ (US); Sriram Natarajan, Hillsborough, NJ (US); Murty N. Vyakarnam, Bridgewater, NJ (US); Chee Tiong Lim, Singapore (SG)

(73) Assignees: ENDO-SURGERY, INC., Cincinnati, OH (US); AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 0 days.

(21) Appl. No.: 13/435,544

(22) Filed: Mar. 30, 2012

(65) Prior Publication Data
US 2012/0251611 A1 Oct. 4, 2012

Related U.S. Application Data (63) Continuation-in-part of application No. 13/340,331, filed on Dec. 29, 2011, which is a continuation-in-part of application No. 12/871,745, filed on Aug. 30, 2010.

(51) Int. Cl.
| | |
|---|---|
| C08G 63/66 | (2006.01) |
| A61K 38/02 | (2006.01) |
| A61K 9/70 | (2006.01) |
| B29C 33/52 | (2006.01) |
| A61L 27/18 | (2006.01) |
| A61L 31/06 | (2006.01) |
| A61B 17/00 | (2006.01) |

(52) U.S. Cl.
CPC .............. *B29C 33/52* (2013.01); *A61L 27/18* (2013.01); *A61L 31/06* (2013.01); *A61B 2017/00871* (2013.01); *A61B 2017/00938* (2013.01); *A61B 2017/00942* (2013.01); *A61B 2017/00951* (2013.01); *Y10T 428/24355* (2015.01)

(58) Field of Classification Search
None
See application file for complete search history.

(56) References Cited

U.S. PATENT DOCUMENTS

| | | | |
|---|---|---|---|
| 4,256,693 | A | 3/1981 | Kondo et al. |
| 4,464,254 | A | 8/1984 | Dojki et al. |
| 4,557,264 | A | 12/1985 | Hinsch |

(Continued)

FOREIGN PATENT DOCUMENTS

| | | |
|---|---|---|
| CN | 101849281 | 9/2010 |
| DE | 4126877 | 11/1992 |

(Continued)

OTHER PUBLICATIONS

Roure et al. "Force mapping in epithelial cell migration". Feb. 15, 2005, PNAS, vol. 102, No. 7, p. 2390-2395.*

(Continued)

*Primary Examiner* — David Sample
*Assistant Examiner* — Donald M Flores, Jr.
(74) *Attorney, Agent, or Firm* — Roberts Mlotkowski Safran Cole & Calderon, P.C.

(57) ABSTRACT

A polydioxanone film comprising substantially cylindrical polydioxanone pillars on at least one side thereof, said pillars having diameters from about 0.2 μm to about 3 μm, and heights from about 2 μm to about 20 μm from the surface of the film, a process for adsorbing proteins using the film and medical devices incorporating the film.

15 Claims, 4 Drawing Sheets

(56) References Cited

U.S. PATENT DOCUMENTS

| | | |
|---|---|---|
| 4,753,776 A | 6/1988 | Hillman et al. |
| 4,911,165 A | 3/1990 | Lennard et al. |
| 5,011,494 A | 4/1991 | von Recum et al. |
| 5,176,692 A | 1/1993 | Wilk et al. |
| 5,246,451 A | 9/1993 | Trescony et al. |
| 5,246,666 A | 9/1993 | Vogler et al. |
| 5,324,519 A * | 6/1994 | Dunn et al. ............... 424/426 |
| 5,344,611 A | 9/1994 | Vogler et al. |
| 5,352,229 A | 10/1994 | Goble |
| 5,455,009 A | 10/1995 | Vogler et al. |
| 5,569,272 A | 10/1996 | Reed et al. |
| 5,723,219 A | 3/1998 | Kolluri et al. |
| 6,217,540 B1 | 4/2001 | Yazawa et al. |
| 6,220,453 B1 | 4/2001 | Kitajima et al. |
| 6,267,772 B1 | 7/2001 | Mulhauser et al. |
| 6,368,871 B1 | 4/2002 | Christel et al. |
| 6,403,655 B1 | 6/2002 | Bezwada et al. |
| 6,485,503 B2 | 11/2002 | Jacobs et al. |
| 6,638,284 B1 | 10/2003 | Rousseau et al. |
| 6,703,041 B2 | 3/2004 | Burns et al. |
| 6,720,469 B1 | 4/2004 | Curtis et al. |
| 6,872,439 B2 | 3/2005 | Fearing et al. |
| 6,913,697 B2 | 7/2005 | Lopez et al. |
| 7,074,294 B2 | 7/2006 | Dubrow |
| 7,195,872 B2 | 3/2007 | Agrawal et al. |
| 7,331,199 B2 | 2/2008 | Ory et al. |
| 7,479,318 B2 | 1/2009 | Jagota et al. |
| 7,745,223 B2 | 6/2010 | Schubert et al. |
| 7,754,233 B2 | 7/2010 | Andjelic et al. |
| 7,988,733 B2 | 8/2011 | Shimp et al. |
| 8,133,484 B2 | 3/2012 | Preiss-Bloom et al. |
| 8,307,831 B2 | 11/2012 | Rousseau |
| 2003/0208888 A1 | 11/2003 | Fearing et al. |
| 2004/0076822 A1 | 4/2004 | Jagota et al. |
| 2004/0125266 A1 | 7/2004 | Miyauchi et al. |
| 2005/0065463 A1 | 3/2005 | Tobinaga et al. |
| 2005/0095699 A1 | 5/2005 | Miyauchi et al. |
| 2005/0106552 A1 | 5/2005 | Ikeda |
| 2005/0181629 A1 | 8/2005 | Jagota et al. |
| 2006/0005362 A1 | 1/2006 | Arzt et al. |
| 2006/0034734 A1* | 2/2006 | Schubert et al. ............ 422/101 |
| 2006/0078724 A1 | 4/2006 | Bhushan et al. |
| 2006/0087053 A1 | 4/2006 | O'Donnell et al. |
| 2006/0154063 A1 | 7/2006 | Fujihara et al. |
| 2006/0204738 A1* | 9/2006 | Dubrow et al. ........... 428/292.1 |
| 2007/0227967 A1 | 10/2007 | Sakaino et al. |
| 2007/0299542 A1 | 12/2007 | Mathisen et al. |
| 2008/0124246 A1 | 5/2008 | Diaz-Quijada et al. |
| 2008/0217180 A1 | 9/2008 | Doye et al. |
| 2008/0241512 A1 | 10/2008 | Boris et al. |
| 2008/0241926 A1* | 10/2008 | Lee et al. .................... 428/409 |
| 2008/0280085 A1 | 11/2008 | Livne |
| 2009/0130372 A1 | 5/2009 | Fukui et al. |
| 2009/0318843 A1 | 12/2009 | Van Holten et al. |
| 2010/0098909 A1 | 4/2010 | Reyssat et al. |
| 2010/0137903 A1 | 6/2010 | Lee et al. |
| 2010/0249913 A1 | 9/2010 | Datta et al. |
| 2011/0021965 A1 | 1/2011 | Karp et al. |
| 2011/0063610 A1 | 3/2011 | Ivanov et al. |
| 2011/0160869 A1 | 6/2011 | Duch et al. |
| 2011/0172760 A1 | 7/2011 | Anderson |
| 2011/0177288 A1 | 7/2011 | Bhushan et al. |
| 2011/0178535 A1 | 7/2011 | Whitman |
| 2011/0282444 A1 | 11/2011 | Liu et al. |
| 2011/0293667 A1 | 12/2011 | Baksh et al. |
| 2012/0052234 A1 | 3/2012 | Natarajan et al. |
| 2012/0143228 A1 | 6/2012 | Natarajan et al. |
| 2012/0251611 A1 | 10/2012 | Luong-Van et al. |
| 2012/0302427 A1 | 11/2012 | Elmouelhi et al. |
| 2012/0302465 A1 | 11/2012 | Elmouelhi et al. |
| 2013/0172927 A1 | 7/2013 | Natarajan et al. |
| 2013/0206330 A1 | 8/2013 | Natarajan et al. |
| 2013/0266761 A1 | 10/2013 | Ho et al. |
| 2013/0267880 A1 | 10/2013 | Luong-Van et al. |
| 2013/0288225 A1 | 10/2013 | Elmouelhi et al. |
| 2014/0120314 A1 | 5/2014 | Ho et al. |

FOREIGN PATENT DOCUMENTS

| | | |
|---|---|---|
| DE | 19832634 A1 | 1/2000 |
| EP | 0358372 A1 | 3/1990 |
| EP | 1416303 | 5/2004 |
| EP | 2062611 A1 | 5/2009 |
| JP | 2004170935 A | 6/2004 |
| JP | 2013-226413 A | 11/2013 |
| JP | 2013/226413 A | 11/2013 |
| SG | 193370 A | 10/2013 |
| WO | 0056808 | 9/2000 |
| WO | 03/099160 A1 | 12/2003 |
| WO | 2004094303 | 11/2004 |
| WO | 2006031197 | 3/2006 |
| WO | 2008/076390 A2 | 6/2008 |
| WO | 2008/076390 A3 | 6/2008 |
| WO | 2008102620 | 8/2008 |
| WO | 2009022911 | 2/2009 |
| WO | 2009029045 | 3/2009 |
| WO | 2009/067482 A1 | 5/2009 |
| WO | 2009123739 A1 | 10/2009 |
| WO | 2010033725 A2 | 3/2010 |
| WO | 2010/129641 A1 | 11/2010 |
| WO | 2011/026987 A1 | 3/2011 |
| WO | WO 2012/030570 A1 | 3/2012 |
| WO | WO 2012/162452 A2 | 11/2012 |
| WO | WO 2013/102085 A1 | 7/2013 |
| WO | 2013/163304 A1 | 10/2013 |

OTHER PUBLICATIONS

Oxford Dictionary Online, "cylinder". <http://oxforddictionaries.com/definition/english/cylinder?q=cylinder> (see attached pdf file).*

[NPL #1] Saez, et al. "Rigidity-driven growth and migration of epithelial cells on microstructured anisotropic substrates". (May 15, 2007), Proceeding of the National Academy of Sciences of the United States (PNAS), vol. 104, No. 20, pp. 8281-8286.*

U.S. Appl. No. 12/871,745, filed Aug. 30, 2010.
U.S. Appl. No. 13/340,331, filed Dec. 29, 2011.
U.S. Appl. No. 13/340,405, filed Dec. 29, 2011.
U.S. Appl. No. 13/116,721, filed May 26, 2011.
U.S. Appl. No. 13/441,496, filed Apr. 6, 2012.
U.S. Appl. No. 13/441,539, filed Apr. 6, 2012.
U.S. Appl. No. 13/458,825, filed Apr. 27, 2012.
Anthony G. Gristina, "Biomaterial-Centered Infection: Microbial Adhesion Versus Tissue Integration", Science, vol. 237, pp. 1588-1595 (1987).
International Search report for International Application No. PCT/US2011/048584 dated Feb. 20, 2012.
International Search report for International Application No. PCT/US2012/072081 dated Mar. 12, 2013.
Definition of "Integral", Merriam-Webster Dictionary online, pp. 1-3, Accessed Oct. 15, 2013.
S.D. Lee, "Surface Modification of Polypropylene Under Argon and Oxygen-RF-Plasma Conditions", Plasmas and Polymers, vol. 2, No. 3, Sep. 1, 1997, pp. 177-198.
International Search Report for PCT/US2013/038007 dated Jun. 18, 2013.
International Search Report for PCT/US2012/039256 dated Mar. 5, 2013.
Wan Y., et al., "Characterization of surface property of poly (lactide-co-glycolide) after oxygen plasma treatment", Biomaterials, Elsevier Science Publishers, vol. 25, No. 19, Aug. 1, 2004, pp. 4777-4783.
Jianhua Wei, et al., "Influence of surface wettability on competitive protein adsorption and initial attachment of osteoblasts; Competitive protein adsorption and initial cell attachment", Biomedical Materials, Institute of Physics Publishing, vol. 4, No. 4, Aug. 1, 2009, p. 45002.

(56) References Cited

OTHER PUBLICATIONS

Tsougeni K., et al., "Mechanisms of oxygen plasma nanotexturing of organic polymer surfaces: From stable super hydrophilic to super hydrophobic surfaces", Langmuir, American Chemical Society, vol. 25, No. 19, Oct. 6, 2009, pp. 11748-11759.
Messina G.M.L., et al., "A multitechnique study of preferential protein adsorption on hydrophobic and hydrophilic plasma-modified polymer surfaces", Colloids and Surfaces. B., Biointerfaces, vol. 70, No. 1, Apr. 1, 2009, pp. 76-83.
Chen H. et al., "The effect of surface microtopography of poly (dimethylsiloxane) on protein adsorption, platelet and cell adhesion", Colloids and Surfaces. B., Biointerfaces, vol. 71, No. 2, Jul. 1, 2009, pp. 275-281.
Search Report of Singapore Patent Application No. 2013086434 dated Dec. 4, 2014.
Written Opinion of Singapore Patent Application No. 2013086434 dated Jan. 16, 2015.
Chang, T.C., Plasma Surface Treatment in Composites Manufacturing, Journal of Industrial Technology, Nov. 1, 1998-Jan. 1999, vol. 15, No. 1, pp. 1-7, Table 1.
Office Action dated May 22, 2015 in U.S. Appl. No. 13/116,721; 27 pages.
Office Action dated May 22, 2015 in U.S. Appl. No. 13/340,405; 30 pages.
Notice of Allowance dated Aug. 6, 2015 in U.S. Appl. No. 13/841,561; 4 pages.
Office Action dated Jun. 4, 2015 in U.S. Appl. No. 13/730,259; 11 pages.
Sriram Natarajan, U.S. Appl. No. 12/871,745, filed Aug. 30, 2010.
Noha Elmouelhi, U.S. Appl. No. 13/116,721, filed May 26, 2011.
Sriram Natarajan, PCT No. PCT/US2011/048,584 Filed Aug. 22, 2011.
Sriram Natarajan, U.S. Appl. No. 13/340,331, filed Dec. 29, 2011.
Noha Elmouelhi, U.S. Appl. No. 13/340,405, filed Dec. 29, 2011.
Emma Kim Luong-Van, U.S. Appl. No. 13/435,544, filed Mar. 30, 2012.
Audrey Yoke Yee Ho, U.S. Appl. No. 13/441,496, filed Apr. 6, 2012.
Emma Kim Luong-Van, U.S. Appl. No. 13/441,539, filed Apr. 6, 2012.
Noha Elmouelhi, U.S. Appl. No. 13/458,825, filed Apr. 27, 2012.
Sriram Natarajan, U.S. Appl. No. 13/730,259, filed Dec. 28, 2012.
Sriram Natarajan, PCT No. PCT/US2012/072081 filed Dec. 28, 2012.
Sriram Natarajan, U.S. Appl. No. 13/841,561, filed Mar. 15, 2013.
Noha Elmouelhi, PCT No. PCT/US2013/038007 filed Apr. 24, 2013.
Sitti, "High Aspect Ratio Polymer Micro/Nano-Structure Manufacturing using Nanoembossing, Nanomolding and Directed Self-Assmbly", IEEE/ASME Advanced Mechatronics Conference, Kobe, Japan, Jul. 2003 (5 pages).
Tsougeni, et al. "Nano-texturing of poly (methyl methacrylate) polymer using plasma processes and applications in wetting control and protein adsorption", Microelectronic Engineering 86 (2009), pp. 1424-1427.
Vlachopoulou, et al., "Effect of surface nanostructuring of PDMS on wetting properties, hydrophobic recovery and protein adsorption", Microelectronic Engineering 86 (2009), pp. 1321-1324.
Gristina, "Biomaterial-Centered Infection: Microbial Adhesion Versus Tissue Integration", Science, vol. 237, Sep. 25, 1987, pp. 1588-1595.
Won, et al., "The Fabrication of Protein Nano Arrays Using 3-Dimensional Plastic Nanopillar Patterns", Journal of Nanoscience and Nanotechnology, 2011, vol. 11, pp. 4231-4235.
Zhao, et al., "Self-organized Polymer Aggregates with a Biomimetic Hierarchical Structure and its Superhydrophobic Effect", Cell Biochem Biophys (2007) 49: pp. 91-97.
Bhushan, et al. "Self-Cleaning Efficiency of Artificial Superhydrophobic Surfaces", Langmuir, 2009, 25, pp. 3240-3248.
Shi, et al., "Communication towards bioinspired superhydrophobic poly (L-lactic acid) surfaces using phase inversion-based methods", Bioinsp. Biomim. 3 (2008) (6 pages).
Jung, et al., "Wetting Behavior of Water and Oil Droplets in Three-Phase Interfaces for Hydrophobicity/philicity and Oleophobicity/philicity", Langmuir 2009, 25 (24), pp. 14165-14173.
Lee, et al., "Fabrication of Heirarchical Structures on a Polymer Surface to Mimic Natural Superhydrophobic Surfaces", Adv. Mater. 2007, 19, pp. 2330-2335.
Cha, et al., "Effect of Replicated Polymeric Substrate with Lotus Surface Structure on Adipose-Derived Stem Cell Behaviors", Macromol. Biosci. 2011, 11, pp. 1357-1363.
Yanagishita, et al., "Anti-Reflection Structures on Lenses by Nanoimprinting Using Ordered Anodic Porous Alumina", Applied Physics Express 2 (2009) (3 pages).
Schulte, et al., "Heirarchically structured superhydrophobic flowers with low hysteresis of the wild pansy (*Viola tricolor*)—new design principals for biomimetic materials", Bellstein J. Nanotechnol. 2011, 2, pp. 228-236.
Bhushan, et al., "Micro-, nano- and Heirarchical structures for superhydrophobicity, self-cleaning and low adhesion", Phil. Trans. R. Soc. A. 2009, 367, pp. 1631-1672.
Occhiello, et al., "Oxygen-Plasma-Treated Polypropylene Interfaces with Air, Water, and Epoxy Resins: Part 1. Air and Water.", 1991, Journal of Applied Polymer Science, 42, pp. 551-559.
Gerard, et al., "Surface modifications of polypropylene membranes used for blood filtration", 2011, Polymer, 52, pp. 1223-1233.
Sriram Natarajan, PCT No. PCT/US2011/048584 Filed Aug. 22, 2011.
Noha Elmouelhi, PCT No. PCT/US2012/039256 filed May 12, 2012.
Audrey Yoke Yee Ho, U.S. Appl. No. 14/139,673, filed Dec. 23, 2013.
European Search Report of European Application No. 12863230.4 dated Jul. 20, 2015.

\* cited by examiner

SUPER-HYDROPHILIC STRUCTURES

This application is a continuation-in-part of, and claims the benefit of priority under 35 U.S.C. §120 to U.S. Ser. No. 12/871,745, filed Aug. 30, 2010, and a continuation-in-part of U.S. Ser. No. 13/340,331, filed Dec. 29, 2011, both of which are incorporated by reference herein in their entireties.

FIELD OF THE INVENTION

The present invention relates to polymer-based structures having shapes and mechanical properties that result in super-hydrophilicity.

BACKGROUND OF THE INVENTION

Biomaterials are being used with increasing frequency for tissue substitution, such as for joint replacements and artificial organs. Tissue integration onto or into these biomaterials enhances long-term biocompatibility of these devices, and requires a form of eukaryocytic adhesion or compatibility with possible chemical integration to an implant surface. However, in what has been characterized as a "race for the surface", bacterial cells are known to compete with tissue cells for colonization onto the surfaces of such biomaterials. If bacterial cells are successful in colonizing an implant surface, devastating infections can occur which can require subsequent surgeries, or even result in sepsis and death, especially in immunosuppressed patients.

In "Biomaterial-Centered Infection: Microbial Adhesion Versus Tissue Integration", by Anthony G. Gristina, *Science*, Vol. 237, pp. 1588-1595 (1987), the author discusses the details of biological attraction and adhesion to various biomaterial implants and concludes that an optimum mechanism for preventing bacterial infection on such surfaces would be to develop biomaterial surfaces which encourage rapid eukaryocytic colonization of the surface, so as to impart the benefits of naturally derived antibacterial mechanisms produced by the living cells adhered to the surface.

There is an ongoing need for polymer-based structures having improved adsorption of biologics, e.g., proteins. Such structures can be suited for use in various applications, such as medical applications, e.g., medical diagnostics. It is especially desirable to provide structures whose surfaces have a specific, finely-tuned adsorption of biological materials.

U.S. Pat. No. 5,246,451 discloses a vascular prosthesis made by coating a vascular graft material such as polyethylene terephthalate plasma coated with a fluoropolymer (PTFE) which is then treated with a plasma in a non-polymerizing gas atmosphere, e.g., oxygen, to improve biological entity binding to the fluoropolymer. The products of this disclosure rely on plasma treatment to improve protein binding and lack modified topography.

U.S. Pat. No. 7,195,872 teaches providing substrates of high surface area with structural microfeatures that provide access to fluids and components therein. The substrates can be prepared by molding, embossing, photoresist techniques and can also be treated by etching, e.g., with argon, oxygen, helium, chlorine, $SF_6$, $CF_4$, and $C_4F_8$ gases. Surfaces can be modified by chemical treatments or radiative treatments, e.g., plasma treatment in gases. The reference emphasizes topography alone to bind proteins, or alternately, additional treatment with oxygen plasma to etch the surface and ammonia plasma for grafting amine groups on the surface.

U.S. Patent Publication No. 2006/0154063 discloses a composite nanofiber construct comprising: at least a first nanofiber comprising at least a polymer and at least a calcium salt nanoparticle, wherein the ratio of polymer to calcium salt nanoparticle is between the range of 99:1 and 10:90 weight percent; and at least a second nanofiber comprising at least a polymer and at least a calcium salt nanoparticle, wherein the ratio of polymer to calcium salt nanoparticle is between the range of 100:0 and 70:30 weight percent. Hydrophilicity of the nanofibers is enhanced by plasma treatment, which lead to good adhesion and growing of cells.

U.S. Patent Publication No. 2008/0241512 discloses a chemical vapor deposition method of depositing layers of materials to provide super-hydrophilic surface properties, or super-hydrophobic surface properties, or combinations of such properties at various locations on a given surface. The invention also relates to electronic applications which make use of super-hydrophobic surface properties, and to biological applications which make use of super-hydrophilic surface properties.

It would be desirable to provide a highly hydrophilic surface structure which does not require a separate treatment step to enhance its hydrophilicity.

It would be further desirable to provide wettable polymer-based structures of substantially fixed topography having controllable adsorption of biologics, e.g., proteins, by adjusting characteristics of a substrate to provide a topography of enhanced surface area that is relatable or proportional to the surface adsorption of a biologic material.

SUMMARY OF THE INVENTION

The present invention relates to a polydioxanone film comprising substantially cylindrical polydioxanone pillars on at least one side thereof, said pillars having a diameter from about 0.6 µm to about 3 µm, and a height of up to about 20 µm from the surface of the film.

In another embodiment, the invention is directed to a process for adsorbing proteins, comprising exposing a protein-containing solution to a polydioxanone film comprising substantially cylindrical polydioxanone pillars on at least one side thereof, said pillars having a diameter from about 0.6 µm to about 3 µm, and a height of up to about 20 µm from the surface of the film.

In a further embodiment, the invention is directed to a medical implant comprising a polydioxanone film comprising substantially cylindrical polydioxanone pillars on at least one side thereof, said pillars having a diameter from about 0.2 µm to about 3 µm, and a height of up to about 20 µm from the surface of the film.

DETAILED DESCRIPTION

The present invention is directed to high aspect ratio (HAR) polydioxanone (PDO) film having surface microstructures which demonstrates super-hydrophilic wetting characteristics, having an inherent static water drop contact angle of less than about 10°. It has been discovered that the super-hydrophilic nature of these structures enhances biologics, particularly protein adsorption onto the surfaces thereof.

The materials of the present invention are useful in various applications relying on biologic adsorption, e.g., protein adsorption, including diagnostic tests and other medical uses such as anastomosis devices, grafts, vascular prosthetic devices, soft tissue implants.

Biologics, for present purposes, include sugars, proteins, lipids, nucleic acids, polynucleotides or complex combinations of these substances, as well as living entities such as cells and tissues. Biologics can be isolated from a variety of natural sources—human, animal, or microorganism—and may be produced by biotechnology methods and other technologies. In some instances, biologics can be prepared using non-biological, chemical methods. Biologics include a wide range of medicinal products such as vaccines, blood and blood components, allergenics, somatic cells, gene therapy, tissues, and recombinant therapeutic proteins created by biological processes (as distinguished from chemistry).

Biologic adsorbent material made from polymer or comprising polymer can be formed into structures having high surface area topography. Structures can have tailored geometric features including substructures, e.g., pillars, with a diameter from 0.1-50 micrometers (100-50000 nm) and height greater than 1 micrometer (>1000 nm), which provide surface area greater than that of a substrate comprised of exposed flat surfaces. Protein adsorbency of a substrate is not dependent on surface area alone. It has now been found that in order to effectively utilize increased surface area of a substrate, adsorption by the substrate surface comprising substructures can be optimized to improve hydrophilicity/ wettability. The polymeric structures according to the present invention of desirable high surface area topography exhibit improved biologics adsorption even without treating of the surfaces, e.g., by oxygen plasma.

In one aspect the present invention relates to a super-hydrophilic structure having a PDO film surface from which extend substantially cylindrical pillar-like protrusions, which protrusions are of sufficiently low diameter to promote adsorption of naturally occurring proteins. Advantageously, the pillars have average diameters ranging from about 0.1 to about 3 micrometers, average lengths (or heights) greater than about 1 micrometer and aspect ratios (length/diameter) of from about 1 to 33. More preferably, the pillars have average diameters ranging from about 0.2 to about 1 micrometer, average lengths greater than about 3 micrometers and aspect ratios (length/diameter) of from about 2 to 30.

Preferably, the PDO pillars have average diameters from about 0.2 micrometer to about 1 micrometer, and heights of about 2 micrometers to about 20 micrometers from the surface of the PDO film. In particular, when the PDO pillars have average diameters from about 0.6 micrometer to about 1 micrometer, and heights of about 20 micrometers from the surface of the PDO film, the film has been found to demonstrate super-hydrophilicity, i.e. static water drop wetting angles of less than about 10°, in the absence of any post-treatment of the film/pillar surfaces. However, post-treatment by such as oxygen plasma treatment can be optionally performed to enhance the hydrophilicity of larger diameter pillars, such as those having average diameters of about 3 micrometers.

In still another embodiment, the super-hydrophilic structure is integrally molded from a PDO resin or polymer, which is thermoplastic. By integrally molded is meant that the structure is formed in one piece, including its protrusions, from a mold. For present purposes, thermoplastic resin or polymer is a resin or polymer that softens when heated and hardens again when cooled.

In yet still another embodiment, the super-hydrophilic structure surface is substantially planar and the pillars are within ±45 degrees of normal to the planar surface, preferably within ±30 degrees of normal to the planar surface In another embodiment, the super-hydrophilic structure has a pillar density of from $1 \times 10^5$ to $6 \times 10^8$ pillars/cm$^2$. For present purposes, "pillar density" can be described as the number of pillars present per square centimeter of super-hydrophilic structure surface. For example, the super-hydrophilic structure has a density of pillars on its surface ranging from about $1 \times 10^7$ to about $5 \times 10^7$ pillars per cm$^2$.

In yet another embodiment, the super-hydrophilic structure has a protein adsorption capacity from about 2.5 µg/cm$^2$ to about 6.0 µg/cm$^2$, or from about 4.0 µg/cm$^2$ to about 6.0 µg/cm$^2$ of the film surface.

The super-hydrophilic structure of the present invention can be at least partially formed by a process selected from nano- or micro-molding using a template, polymer self-assembly, lithography, and etching.

In another embodiment, the invention is directed to a process for adsorbing proteins, comprising exposing a protein-containing solution to a polydioxanone film comprising substantially cylindrical polydioxanone pillars on at least one side thereof, said pillars having diameters from about 0.2 µm to about 3 and heights of about 2µm to about 20 µm from the surface of the film. Optionally, the pillars are treated with an oxygen plasma to increase the oxygen content of the pillars, relative to untreated polydioxanone pillars.

In a further embodiment, the invention is directed to a medical device comprising a polydioxanone film comprising substantially cylindrical polydioxanone pillars on at least one side thereof, said pillars having diameters from about 0.2 µm to about 3 and heights from about 2 µm to about 20 µm from the surface of the film. The medical devices can include medical implants, for example, anastomosis devices, grafts, vascular prosthetic devices and soft tissue implants.

The method for preparing a super-hydrophilic structure comprises: a) providing a specific solvent-dissolvable mold including pores or indentations; b) providing a meltable PDO polymer to the mold under conditions sufficient to permit filling the indentations of the mold by the polymer, said polymer being substantially non-dissolvable by the specific solvent; c) treating the mold and polymer of step b) to an extent sufficient to substantially solidify the polymer; and d) exposing the mold and polymer to the specific solvent under mold-dissolving conditions to provide a molded polymer substrate material comprising protrusions or pillars conforming to the indentations or pores of the mold. Optionally, this aspect further comprises at least one of the following conditions:

i) wherein the meltable polymer is provided to the mold as a softened film;
  ii) wherein the mold comprises polycarbonate, the polymer is polydioxanone and the solvent is dichloromethane; and iii) wherein step b) is carried out in a first stage and second stage, wherein the second stage is carried out at a greater pressure.

In one embodiment, the first stage is carried out at a temperature ranging from 90 to 110° C., pressure ranging from about 0 to about 20 kPa (about 0 to about 0.2 Bar), for a duration of 7 to 12 minutes, and the second stage is carried out at a temperature ranging from 90 to 110° C., pressure ranging from about 6 to about 20 kPa (about 0.06 to about 0.2 Bar), for a duration of 15 to 25 minutes.

Optionally, in order to further enhance hydrophilicity, the PDO pillars and film surface can be treated with oxygen plasma, such as at 50 to 150 watts for 15 to 45 seconds, or at 75 to 125 watts for 25 to 35 seconds.

The invention is further explained in the description that follows with reference to the drawings illustrating, by way of non-limiting examples, various embodiments of the invention.

Example 1

A 100 micrometers thick polydioxanone film with pillar-like structures on both sides was prepared. A polydioxanone film was compressed under heat and pressure between two 20 micrometers thick sheets of polycarbonate filter material. The filter material possesses microscopic (0.8 micrometer) holes. The polydioxanone film melted and flowed into the holes. After processing the sheet was annealed. The polycarbonate membrane filter was then dissolved in a bath of dichloromethane. The membrane filters used (0.8 micrometer ATTP, Cat No. ATTP14250, Lot No. R9SN70958 available from Millipore Corporation of Billerica, Mass., USA) possessed two distinct sides. One side had a shiny appearance while the other was duller. A laminate for compression molding was constructed as follows:
- a. A segment of polyimide film (sold under the tradename KAPTON by DuPont, Wilmington, Del.) of 65-70 micrometers thickness was placed on a table;
- b. A 15.2 cm (6 inch) polished square metal plate (thickness 0.8 mm) (shiny side up) was placed on the polyimide film;
- c. A segment of polyimide film was placed on the 15.2 cm (6 inch) plate;
- d. A 15.2 cm×15.2 cm (6"×6")×80 micrometers steel shim with a 10.1 cm×10.1 cm (4"×4") cavity in the center was placed on the film;
- e. A membrane filter was cut to fit in the shim cavity and was placed (dull side up) on the polyimide film;
- f. A piece of 25 micrometers thick polydioxanone film was cut to fit in the shim cavity. The sample was placed on the membrane;
- g. Another membrane filter (about 20 micrometers thick) was cut to fit in the shim cavity and placed (dull side down) on the polydioxanone film;
- h. A segment of polyimide film was placed on the top membrane;
- i. A 15.2 cm (6 inch) polished square metal plate (thickness 0.8 mm) (shiny side down) was placed on the polyimide film; and
- j. Another segment of polyimide film was placed on the steel plate.

The resulting sample was loaded into a heated press with vacuum (less than 150 micrometers mercury) capability and was processed as follows:
- a. The top and bottom platens were preheated to 220° C. (428° F.);
- b. The sample was preheated under vacuum for 300 seconds prior to any compression;
- c. The sample was compressed at 68948 kPa (10,000 psi) for 300 seconds;
- d. The temperature was reduced to 21° C. (70° F.) while maintaining compression of 68948 kPa (10,000 psi);
- e. The compressive force was released and the vacuum was purged; and
- f. The sample was removed from the vacuum press.

The sample was annealed in the constrained condition (between two steel plates) in an inert environment (nitrogen gas) for a minimum of six hours at 70° C.

The polycarbonate membrane had been fused to the surface of the polydioxanone film. The membrane was removed from the surface of the polydioxanone film by immersing the sample in a bath of dichloromethane at room temperature for five minutes and was allowed to air dry prior to handling. Scanning electron microscope (SEM) images of the sample confirmed the presence of pillar-like structures which were about 20 micrometers high and 0.8 micrometer in diameter.

Example 2

PDO pillars of 0.6, 1, and 3 micrometer diameters and heights of 20 micrometers were fabricated on PDO film essentially by the method set forth in Example 1, using commercial track etched polycarbonate membranes as a mold and a nanoimprinting process. Membranes having pores of 0.6 and 1 micrometer diameters and circular diameters of 4.5 cm, with thicknesses of 20 micrometers were obtained from Whatman, Florham Park, N.J. Membranes having pores of 3 micrometers diameter and circular diameters of 4.5 cm, with thicknesses of 20 micrometers were obtained from Millipore Corporation of Billerica, Mass., USA. The membranes were used as templates to imprint a solvent-resistant PDO polymer film of 0.3 millimeter thickness, obtained from Ethicon, Inc. of Somerville, N.J., USA. The PDO film was pressed into the polycarbonate membrane templates under high temperature and pressures (120° C., 6000 kPa (60 bar)) for 5 minutes, melting the PDO. The PDO films with the imprinted PC membrane were placed between 2 metal plates and annealed for 3 hours at 70° C. The polymer structures were de-molded and released by dissolving the polycarbonate membrane in dicholoromethane. Films were immersed in two consecutive dichloromethane baths for 5 minutes per wash and then air dried.

Figure 1:
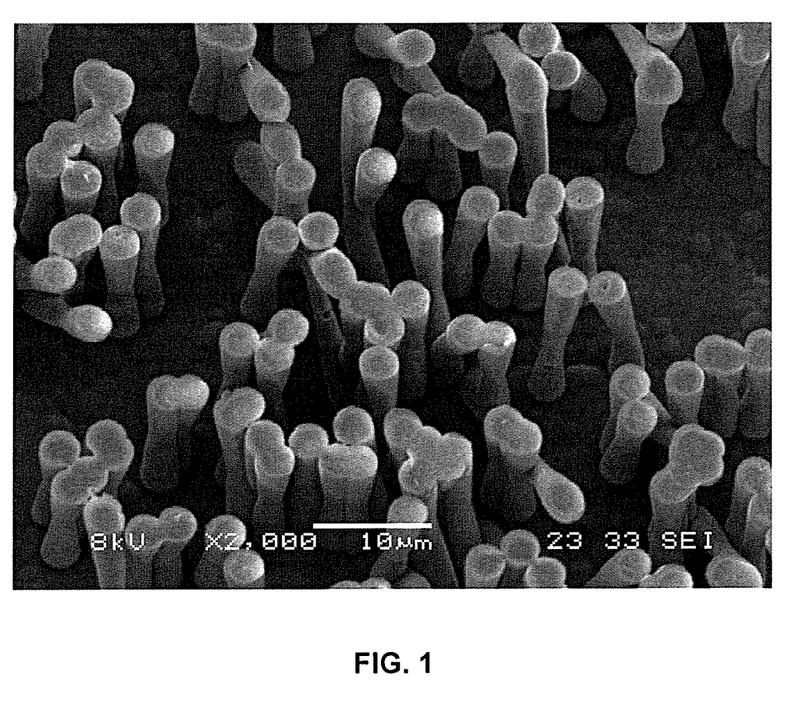
FIG. 1 is a scanning electron microscope image of a super-hydrophilic PDO film having 3 micrometer pillars extending from the surface of the film.
Figure 2:
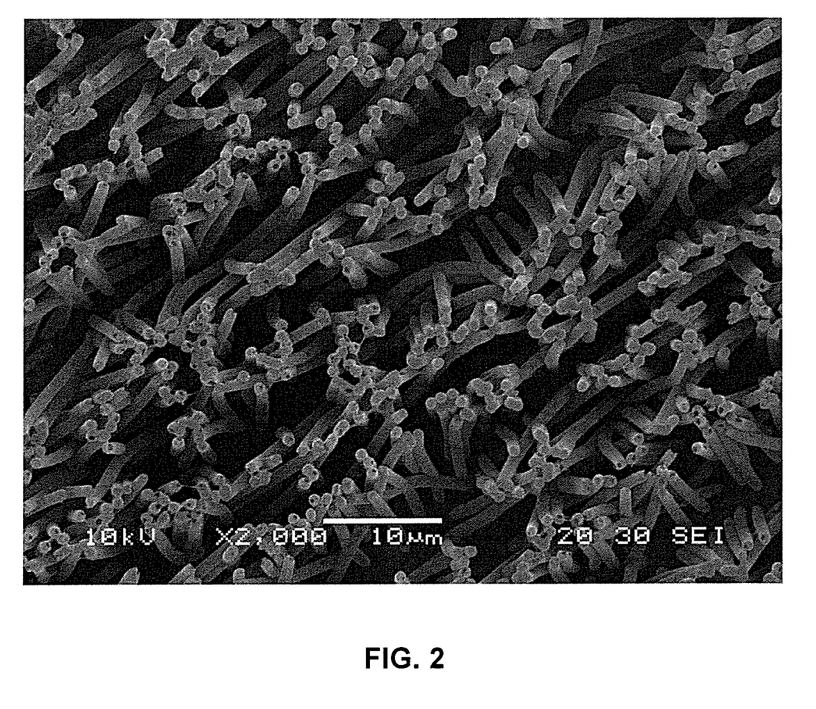
FIG. 2 is a scanning electron microscope image of a super-hydrophilic PDO film having 1 micrometer pillars extending from the surface of the film.
Figure 3:
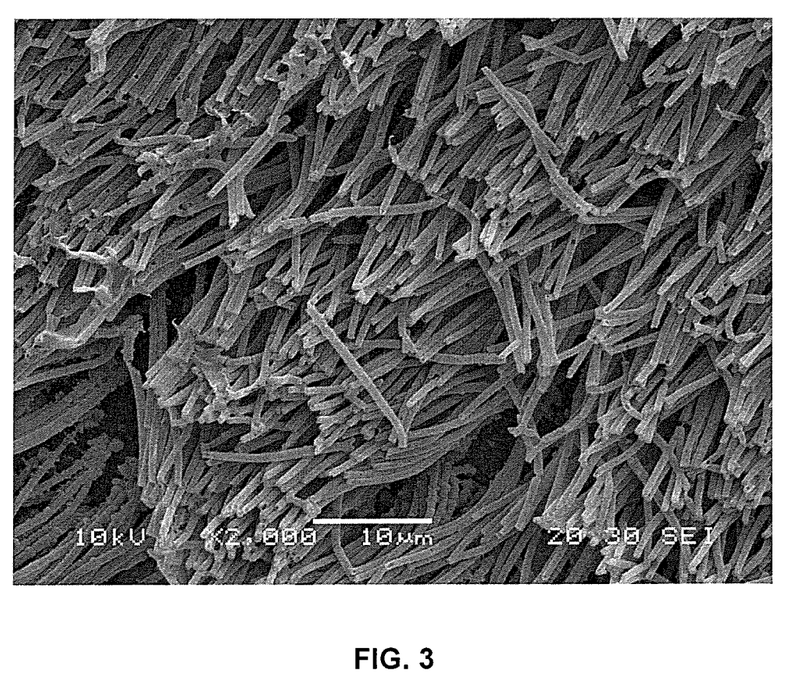
FIG. 3 is a scanning electron microscope image of a super-hydrophilic PDO film having 0.6 micrometer pillars extending from the surface of the film.

Scanning electron microscope (SEM) images of the samples confirmed the presence of pillar-like structures which were about 20 micrometers high. FIGS. 1, 2, and 3, depict SEM images of the 3 um diameter, 1 um diameter, and 0.6 um diameter HAR pillars, respectively.

The surface area ratio for these structures is more than 2 times the surface area of a flat film as shown in Table 1 below.

TABLE 1

|  | Flat film | 3 μm HAR pillars | 1 μm HAR pillars | 0.6 μm HAR pillars |
| --- | --- | --- | --- | --- |
| Surface Area Ratio | 1 | 2 | 5 | 8 |

The surfaces of the PDO films were treated by oxygen plasma treatment using a microwave plasma processor (100 W, 30 seconds). Surface elemental analysis was conducted on the flat PDO films to determine the oxygen content of the film surfaces both before and after oxygen plasma treatment. The results are set forth in Table 2 below.

TABLE 2

| Element | Untreated PDO | Plasma-Treated PDO |
|---------|---------------|--------------------|
| C | 55.5% | 54.4% |
| O | 38.1% | 42.1% |

Static water contact angle measurements, herein referred to as contact angle measurements, were conducted using a sessile drop method. A Rame-Hart contact angle goniometer with Drop Image software was used. Plasma treatment was done immediately before contact angle measurement. Two microliter drops of de-ionized water were placed on the surface for measurement, and 5 measurements were taken for each surface. The mean contact angles are reported in Table 3.

TABLE 3

| | Contact Angle Untreated | Contact Angle Plasma-Treated |
|---|---|---|
| Flat film | 80° | 14° |
| 3 μm HAR pillars | 95° | spreads* |
| 1 μm HAR pillars | spreads | spreads |
| 0.6 μm HAR pillars | spreads | spreads |

*indicative of a contact angle of less than 10°

Pillars with diameters 0.6 and 1 micrometer were wettable even without oxygen plasma treatment. The contact angle of PDO surfaces patterned with 3 um pillars increased slightly compared to the flat film. Oxygen plasma treatment increased the wettability of the flat and 3 um pillar surfaces.

The protein adsorption or protein uptake properties of these samples were evaluated by incubating the samples in protein solution and assaying using the bicinchoninic acid (BCA) assay. Films were cut into 1×1 cm pieces and incubated in 1 ml of fibrinogen protein solution (2 mg/ml in phosphate buffered saline (PBS)) in a sealed 24-well plate overnight (18 hrs) with orbital shaking. After protein incubation the films were removed from the wells and washed in 3 consecutive baths of PBS and then immediately quantified using the BCA Assay.

The BCA assay was conducted as follows: protein standards were made using the bovine serum albumin (BSA) standard provided in the BCA kit (QuantiPro BCA kit, Sigma Aldrich). Rinsed films were placed in wells of a 24-well plate containing 500 microliters PBS+500 microliters BCA reagent (prepared as per kit instructions). For protein standards, 500 microliters of protein standard solution was placed in the well with 500 microliters BCA reagent. The plate was sealed and protected from light and incubated with orbital shaking at 50 rpm for 2 hrs at 37° C. After incubation, 200 microliters of the solution was transferred to wells of 96-well plate for absorbance reading at 562 nm.

Figure 4:
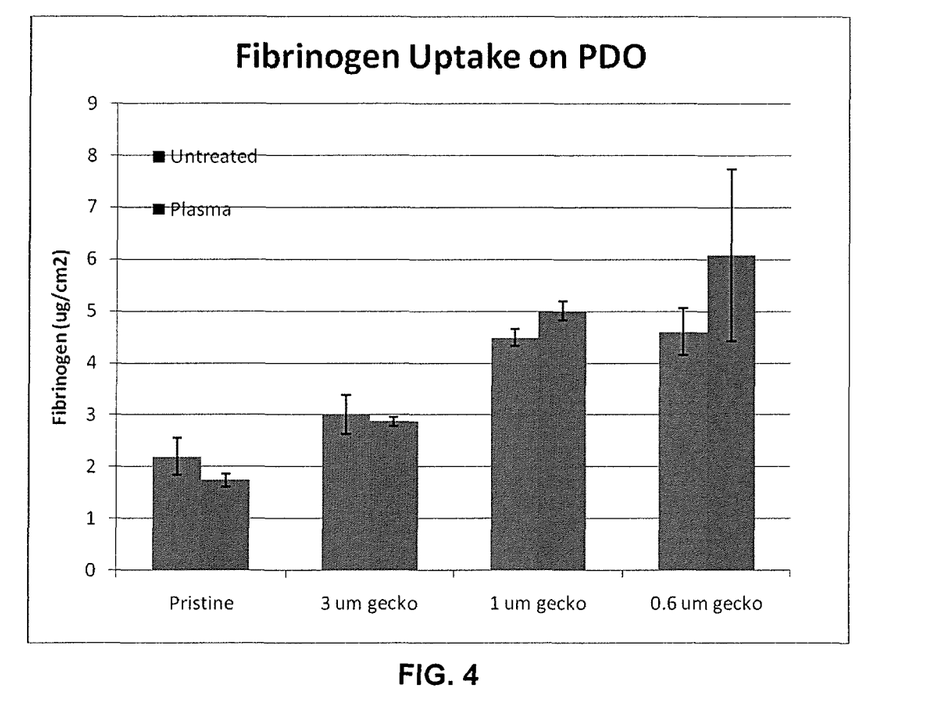
FIG. 4 is a graph comparing the protein (fibrinogen) adsorption capacities of the various embodiments of the invention, as compared to a flat film.

Increasing levels of fibrinogen adsorption were observed as the surface area of the sample increases. This trend was observed for both untreated and plasma-treated HAR pillar samples, since both exhibit similar water contact angle profiles. This trend was observed for fibrinogen as shown in FIG. 4.

All patents, test procedures, and other documents cited herein, including priority documents, are fully incorporated by reference to the extent such disclosure is not inconsistent and for all jurisdictions in which such incorporation is permitted.

When numerical lower limits and numerical upper limits are listed herein, ranges from any lower limit to any upper limit are contemplated.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

What is claimed:

1. A polydioxanone film comprising polydioxanone pillars having circular cross-sections integrally molded with and extending from the surface of at least one side of said film, said pillars having diameters from about 0.2 μm to about 3 μm, and heights of from about 2 μm to about 20 μm from the surface of the film, wherein the polydioxanone pillars demonstrate super-hydrophilicity.

2. The polydioxanone film of claim 1, wherein the pillars are treated with an oxygen plasma to increase the oxygen content of said polydioxanone pillars, relative to untreated polydioxanone pillars.

3. The polydioxanone film of claim 2, wherein the polydioxanone pillars have heights of about 20 μm from the surface of the film, having a static water contact angle of less than about 10°.

4. The polydioxanone film of claim 1, wherein the polydioxanone pillars have diameters from about 0.6 μm to about 1 μm, heights of about 20 μm from the surface of the film, having a static water contact angle of less than about 10°.

5. The polydioxanone film of claim 1, which has a protein adsorption capacity from about 2.5 $\mu g/cm^2$ to about 6.0 $\mu g/cm^2$ of the film surface.

6. The polydioxanone film of claim 5, which has a protein adsorption capacity from about 4.0 $\mu g/cm^2$ to about 6.0 $\mu g/cm^2$ of the film surface.

7. A process for adsorbing proteins, comprising exposing a protein-containing solution to a polydioxanone film comprising polydioxanone pillars having circular cross-sections integrally molded with and extending from the surface of at least one side of said film, said pillars having diameters from about 0.2 μm to about 3 μm, and heights from about 2 μm to about 20 μm from the surface of the film, wherein the polydioxanone pillars demonstrate super-hydrophilicity.

8. The process of claim 7, wherein the pillars are treated with an oxygen plasma to increase the oxygen content of said polydioxanone pillars, relative to untreated polydioxanone pillars.

9. The process of claim 7, wherein the polydioxanone pillars have diameters from about 0.6 μm to about 1 μm, heights of about 20 μm from the surface of the film, having a static water contact angle of less than about 10°.

10. The process of claim 8, wherein the polydioxanone pillars have heights of about 20 μm from the surface of the film, having a static water contact angle of less than about 10°.

11. The process of claim 7, wherein the polydioxanone film has a protein adsorption capacity from about 2.5 $\mu g/cm^2$ to about 6.0 $\mu g/cm^2$ of the film surface.

12. The process of claim 11, wherein the polydioxanone film has a protein adsorption capacity from about 4.0 $\mu g/cm^2$ to about 6.0 $\mu g/cm^2$ of the film surface.

13. A medical device comprising a polydioxanone film comprising polydioxanone pillars having circular cross-sections integrally molded with and extending from the surface of at least one side of said film, said pillars having a diameter from about 0.2 µm to about 3 µm, and a height of up to about 2 µm to about 20 µm from the surface of the film, wherein the polydioxanone pillars demonstrate super-hydrophilicity.

14. The medical device of claim 13, which has improved biocompatibility as compared to an implant device without said film.

15. The medical device of claim 13, which has an increased capacity for protein adsorption as compared to a flat polydioxanone film.

* * * * *